United States Patent
Shechterman

(10) Patent No.: US 9,883,788 B2
(45) Date of Patent: Feb. 6, 2018

(54) PROXIMAL HIGH DEFINITION ENDOSCOPE

(75) Inventor: Mark Shechterman, Ness Ziona (IL)

(73) Assignee: Visionsense Ltd., Petach Tikva (IL)

( * ) Notice: Subject to any disclaimer, the term of this patent is extended or adjusted under 35 U.S.C. 154(b) by 436 days.

(21) Appl. No.: 14/344,429

(22) PCT Filed: Sep. 12, 2012

(86) PCT No.: PCT/IL2012/000339
§ 371 (c)(1),
(2), (4) Date: Mar. 12, 2014

(87) PCT Pub. No.: WO2013/038403
PCT Pub. Date: Mar. 21, 2013

(65) Prior Publication Data
US 2014/0364693 A1    Dec. 11, 2014

Related U.S. Application Data

(60) Provisional application No. 61/534,078, filed on Sep. 13, 2011, provisional application No. 61/693,570, filed on Aug. 27, 2012.

(51) Int. Cl.
*G02B 21/22*    (2006.01)
*A61B 1/00*    (2006.01)
*A61B 1/055*    (2006.01)

(52) U.S. Cl.
CPC .......... *A61B 1/00193* (2013.01); *A61B 1/055* (2013.01)

(58) Field of Classification Search
CPC ..... A61B 1/00193; A61B 1/042; A61B 1/055; A61B 1/0096; A61B 1/0005; A61B 1/002;
(Continued)

(56) References Cited

U.S. PATENT DOCUMENTS 4,815,833 A * 3/1989 Zobel ................... G02B 23/243
                                                   359/726
5,557,454 A * 9/1996 Takahashi .......... A61B 1/00193
                                                   348/45
(Continued)

FOREIGN PATENT DOCUMENTS

| IL | 188169 A | 6/2011 |
|----|----------|--------|
| WO | 9727798 A1 | 8/1997 |
| WO | 2011049195 A1 | 4/2011 |

OTHER PUBLICATIONS

Notification of Transmittal of the International Search Report and the Written Opinion of the International Searching Authority, or the Declaration for PCT/IL2012/000339 dated Mar. 22, 2013, 1 page.
(Continued)

*Primary Examiner* — Bumsuk Won
*Assistant Examiner* — Collin X Beatty
(74) *Attorney, Agent, or Firm* — Brown Rudnick LLP

(57) ABSTRACT

A stereoscopic endoscope pupil configuration for embedding in a stereoscopic endoscope, the shape of the cross section of the stereoscopic endoscope is a predetermined closed two-dimensional shape, the stereoscopic endoscope pupil configuration including at least two pupils, each of the at least two pupils having a shape covering a different unique portion of the two-dimensional closed shape, and together the at least two pupils substantially fully forming the two-dimensional closed shape.

10 Claims, 10 Drawing Sheets

(58) Field of Classification Search
CPC ............... G02B 23/2415; G02B 23/24; G02B 23/2407; G02B 23/2446; G02B 23/2423; G02B 23/243; G02B 27/22; G02B 27/2228; G02B 27/2242; G02B 21/22

USPC ...... 600/111, 130, 166, 138; 348/45, 65, 42; 359/376, 377, 378, 462, 466
See application file for complete search history.

(56) References Cited

U.S. PATENT DOCUMENTS

| | | | |
|---|---|---|---|
| 5,612,816 A * | 3/1997 | Strahle | A61B 1/00193 351/216 |
| 5,689,365 A * | 11/1997 | Takahashi | A61B 1/00179 348/E13.014 |
| 5,743,846 A | 4/1998 | Takahashi et al. | |
| 5,776,049 A | 7/1998 | Takahashi | |
| 5,861,987 A * | 1/1999 | Nakamura | G02B 23/2415 359/429 |
| 5,944,655 A | 8/1999 | Becker | |
| 7,405,877 B1 | 7/2008 | Schechterman | |
| 8,345,084 B2 * | 1/2013 | Namii | A61B 1/00193 348/45 |
| 2002/0082476 A1 | 6/2002 | Takahashi et al. | |
| 2011/0199471 A1 | 8/2011 | Tomioka | |

OTHER PUBLICATIONS

International Search Report for PCT/IL2012/000339 dated Mar. 22, 2013, 2 pages.
Written Opinion for PCT/IL2012/000339 dated Mar. 22, 2013, 6 pages.

* cited by examiner

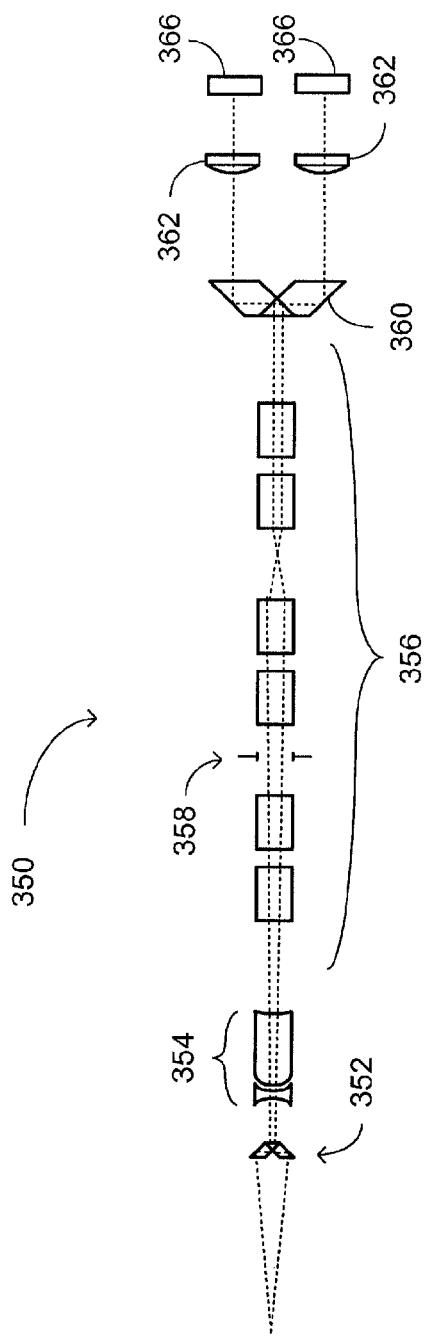
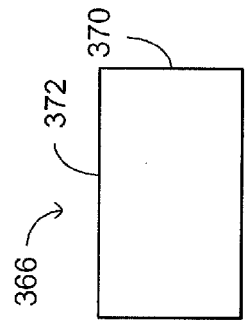
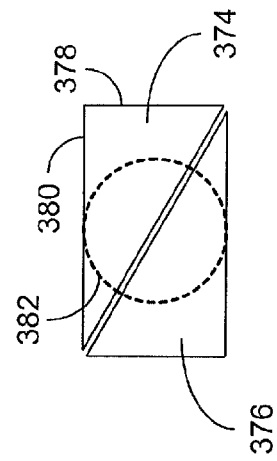
FIG. 6A
FIG. 6B
FIG. 6C

PROXIMAL HIGH DEFINITION ENDOSCOPE

FIELD OF THE DISCLOSED TECHNIQUE

The disclosed technique relates to optical stereoscopic relay systems, in general, and to methods and systems for producing a stereoscopic endoscope having a single axis optical relay system, which images both object and pupils, and further having pupils, which complement each other for substantially forming together the closed shape of the cross section of the relay system, in particular.

BACKGROUND OF THE DISCLOSED TECHNIQUE

Stereoscopic endoscopes are known in the art. The endoscope receives light beams respective of two different perspectives of an object (i.e., stereoscopic image pair), in two distally separated pupils. The endoscope relays each of the images (i.e., of a stereoscopic pair) separately through a respective pair of relay systems, onto a pair of sensors. Each of the sensors detects a different respective image of the object. Each of the object images is presented to a different eye of a user, which constructs a three dimensional representation of the object in her mind. Detailed herein below are several prior art publications which might be relevant for the disclosed technique:

International Patent Application Publication No. WO 97/27798, to Leiner, and entitled "Stereoscopic Endoscope", is directed to a stereoscopic endoscope with two objective lens elements to create left and right images. The endoscope includes two polarizing elements one for each objective lens corresponding to the left and right images. The endoscope further includes rhombic prisms for providing greater parallax.

U.S. Pat. No. 5,944,655, issued to Becker, and entitled "3d Endoscope with Optical Switch and Prism Arrangement", is directed to a 3D-video endoscope with two optical inputs and an electrical output for a video signal. The left and right images are transmitted alternately by using optical switches. The endoscope includes a beam deflecting structure, consists of prisms, through which the picture is passed.

U.S. Pat. No. 5,776,049, issued to Takahashi, and entitled "Stereo Endoscope and Stereo Endoscope Imaging Apparatus", is directed to a stereo endoscope and a stereo imaging apparatus which enable stereo observation of an object by producing a parallax. The stereo endoscope includes a single optical relay system between the objective optical systems and the imagery optical system.

U.S. Pat. No. 7,405,877, issued to Schechterman, and entitled "Stereoscopic Endoscope", is directed at a stereoscopic endoscope having a channel separator employing Total Internal Reflection (TIR) for separating between the different images of the stereoscopic pair (i.e., for channel separation).

U.S. Pat. No. 5,743,846, issued to Takahashi, and entitled "Stereoscopic Endoscope Objective Lens System Having a Plurality of Front Lens Groups and One Common Rear Lens Group" is directed at a stereoscopic endoscope. The endoscope includes an elongate inserted section, an illuminating light system, an objective optical system, and a common relay lens system. The objective system is positioned at the distal end of the inserted section for forming a plurality of images having parallax between them through a plurality of incident pupils. The common relay system transmits the plurality of images to the proximal end of the inserted section. The objective optical system includes a plurality of front lens groups and a rear lens group. The plurality of front lens groups comprise two negative lens units arranged in parallel with each other and the rear lens group comprises a single positive lens group.

SUMMARY OF THE PRESENT DISCLOSED TECHNIQUE

It is an object of the disclosed technique to provide a novel system of a stereoscopic endoscope. In accordance with the disclosed technique there is thus provided a pupil configuration for embedding in a stereoscopic endoscope, having a closed two-dimensional cross section shape. The pupil configuration includes at least two pupils. Each of the pupils has a shape, which covers a different unique portion of the two-dimensional closed shape. The pupils form together substantially fully the two-dimensional closed shape.

In accordance with another aspect of the disclosed technique, there is thus provided a stereoscopic endoscope. The endoscope includes a dual pupil, an optical relay system, two distal periscope prisms, and a distal objective lens assembly. The dual pupil includes a first pupil and a second pupil. The distal objective lens assembly includes a common lens assembly, a first front lens assembly, and a second front lens assembly.

Each of the first pupil and the second pupil receives an image of a respective perspective of an object. The optical relay system is optically coupled with the dual pupil for relaying the respective images of the object. The relay system has a closed two-dimensional cross section shape. The exit surfaces of the two distal periscope prisms are positioned adjacent to each other for complementing each other. The common lens assembly is positioned proximally to the distal periscope prisms. Both the first front lens assembly and the second front lens assembly are positioned distally to the distal periscope prisms. The first pupil and the second pupil complement each other for substantially forming together the two-dimensional closed shape.

BRIEF DESCRIPTION OF THE DRAWINGS

The disclosed technique will be understood and appreciated more fully from the following detailed description taken in conjunction with the drawings in which:

FIG. 6, which is a schematic illustration of a stereoscopic endoscope system, constructed and operative in accordance with another embodiment of the disclosed technique;

DETAILED DESCRIPTION OF THE EMBODIMENTS

The disclosed technique overcomes the disadvantages of the prior art by providing a stereoscopic endoscope, including an optical relay system and an imaging system. The imaging system is positioned outside of the endoscope and therefore can be increased in size and resolution.

The optical relay system includes a pair of distal periscope prisms, which receive light beams reflected from an object from at least two separate perspectives. The distal periscope prisms pair provides the light beams reflected from the object through the relay system to the imaging system. The exit surfaces of the distal prisms are positioned adjacent to each other and complement each other for forming together a closed shape. For example, the exit surfaces of the distal prisms are chamfered, and together form a square shape.

The shape of the cross section of the optical relay system, perpendicular to the optical axis (not shown) of the relay system, is a two dimensional closed shape (e.g., for a cylindrical rod lenses chain the cross section is in the shape of a circle). The pupils of the stereoscopic endoscope complement each other for substantially forming together the closed shape of the cross section of the relay system.

The optical relay system images both object and pupils (i.e., produces intermediate object images and intermediate pupil plane images). The intermediate pupil plane images substantially fully cover the cross section of the optical relay system in at least one location along the relay system.

The pupils of the different channels of the stereoscopic endoscope are separated by a boundary. The boundary between the pupils corresponds to the chamfering of the exit surfaces of the distal prisms. In particular, the chamfering of the exit surfaces of the distal prisms defines the boundary between the pupils. The chamfering of the exit surfaces of the distal prisms and the corresponding inclination angle of the boundary between the pupils, correspond to the required resolution in each of the principal axes of the sensors. That is, the inclination angle defines the ratio between vertical and horizontal dimension of each of the pupils, and thereby defining the resolution in horizontal and vertical directions of the pupils. The inclination angle (i.e., and the exit surfaces chamfering) is determined according to the shape of the sensor. In particular, the ratio between the vertical resolution and the horizontal resolution of the sensors dictates the ratio between the vertical and horizontal dimensions of each of the pupils. It is noted however, that the shape of the pupil is independent of the shape of the sensor.

Figure 1:
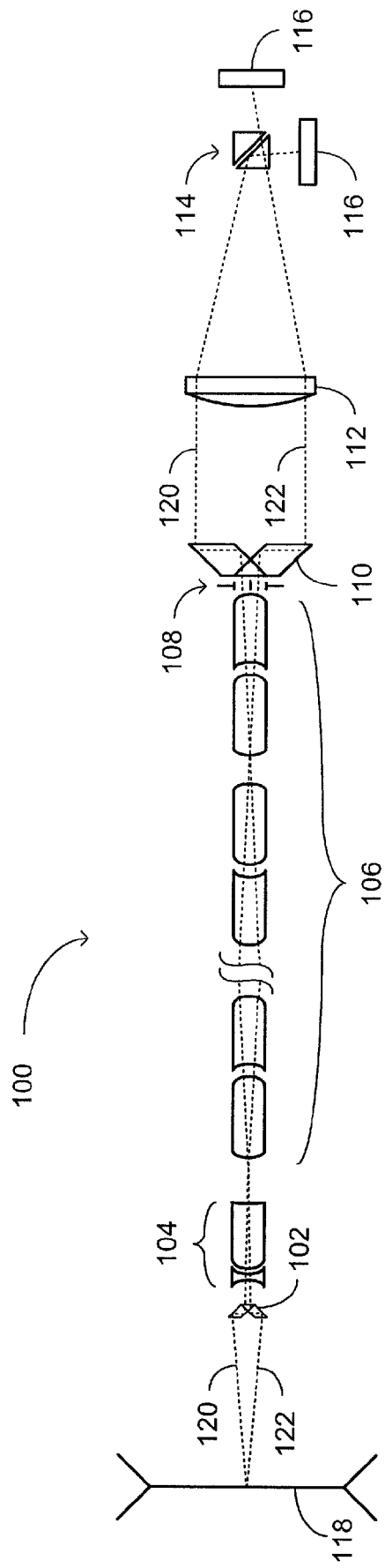
FIG. 1 is a schematic illustration of a stereoscopic endoscope system, constructed and operative in accordance with an embodiment of the disclosed technique.

Reference is now made to FIG. 1, which is a schematic illustration of a stereoscopic endoscope system, generally referenced 100, constructed and operative in accordance with an embodiment of the disclosed technique. Endoscope 100 includes a pair of distal periscope prisms 102, a distal objective lens assembly 104, a rod lenses chain 106, a dual pupil 108, a pair of proximal periscope prisms 110, a proximal objective lens assembly 112, a channel separator 114, and two sensors 116.

Distal objective lens assembly 104 is optically coupled between distal periscope prisms 102 and rod lenses chain 106. Dual pupil 108 is optically coupled between rod lenses chain 106 and proximal periscope prisms 110. Proximal objective lens assembly 112 is optically coupled between proximal periscope prisms 110 and channel separator 114. Channel separator 114 is further optically coupled with each of sensors 116.

An object 118 is positioned distally to distal periscope prisms 102 and is viewed thereby. Object 118 is illuminated by a light source (not shown) either directly or through special means, such as a fibers bundle or a light-guide. Light beams, reflected from object 118, impinge on each of distal periscope prisms 102 and enter endoscope 100 therethrough. In particular, a first distal prism (not referenced) receives light beams respective of a first perspective of object 118, and a second distal prism (not referenced) receives light beams respective of a second perspective of object 118. It is noted that the light beams can be of any spectrum of the electro-magnetic radiation whether visible or not (e.g., visible light, infra-red light, and the like).

Distal periscope prisms 102 transmit the entering light beams onto distal objective lens assembly 104 and afterwards onto rod lenses chain 106 (i.e., onto an optical relay system including objective lens assembly 104 and rod lenses chain 106). The transmitted light beams, after passing through objective lens assembly 104, are associated with a stereoscopic pair of images. In particular, each of the stereoscopic image pair is associated with light beams passing through a different one of distal periscope prisms 102.

Distal periscope prisms 102 create increased Inter-Pupil Distance (IPD) of stereoscopic endoscope 100. In particular, the IPD is the distance between the centers of the pupils re-imaged by distal periscope prisms 102. The structure and operation of distal periscope prisms 102 is further detailed herein below with reference to FIGS. 2A-2E. Distal objective lens assembly 104 includes at least one objective lens for focusing light beams from distal periscope prisms 102 in front of rod lenses chain 106.

The optical relay system is both object imaging and pupil imaging. In particular, rod lenses chain 106 is constructed of repeating sub-chains which produce a series of object images and additionally produce a series of pupil plane images. A re-imaged object relates to a plane perpendicular to the optical axis (not shown) of the optical relay system, in which an image of the object is produced by the optical relay system. A re-imaged pupil plane is a plane perpendicular to the optical axis of the optical relay system, in which the aperture stop is re-imaged. At the re-imaged pupil plane, the light beams from the object are fully separated according to the distal prism through which the light beams entered the relay system. That is, the stereoscopic image pair is fully separated at each of the pupil plane images.

Additionally, the relay system maintains the entering light beams there-within by employing converging and diverging lenses in each of the sub-chains of rod lenses chain 106. Further additionally, rod lenses chain 106 relays the stereoscopic images of object 118 with reduced aberrations. The structure and operation of rod lenses chain are detailed further herein below with reference to FIGS. 4 and 5.

Rod lenses chain 106 transmits the entering light beams through dual pupil 108 and onto proximal periscope prisms 110. Dual pupil 108 is constructed of an aperture stop and an opening (both not shown). The shape of dual pupil 108 (i.e., the shape of the opening of the aperture stop) corresponds to the cross section shape of the optical relay system. Dual pupil 108 includes two pupils defining two channels of endoscope 100. The pupils of dual pupil 108 complement each other for substantially fully covering the opening of dual pupil 108. Thereby the pupils of dual pupil complement each other for substantially forming together the cross section shape of the optical relay system. Each pupil of dual pupil 108 receives light beams respective of a different perspective of object 118 (i.e., light beams entering through a different one of distal periscope prisms 102). In this manner, the single axis relay system, including both distal objective lens assembly 104 and rod lenses chain 106, transmits two images, respective of two perspectives of object 118. The structure and operation of dual pupil 108 is detailed further herein below with reference to FIG. 3.

Proximal periscope prisms 110 receive the entering light beams from dual pupil 108. Proximal periscope prisms 110 transmit the entering light beams onto proximal object lens assembly 112 and channel separator 114. Proximal periscope prisms 110 enlarge the distance between beams from each of the pupils of dual pupil 108 for adjusting the angular and spatial separation between those light beams for purpose of proper beam separation on channel separation 114. Proximal objective lens assembly 112 includes at least one objective lens for focusing beams exiting proximal periscope prisms 112 onto both sensors 116.

Channel separator 114 separates the entering light beams in accordance with the pupil (i.e., of dual pupil 108) through which the light beams passes, thereby separating the stereoscopic images. That is, channel separator 114 directs light beams passing through the first pupil, associated with a first image of the stereoscopic pair, onto a first one of sensors 116. Channel separator 114 directs light beams passing through the second pupil, associated with a second image of the stereoscopic pair, onto a second one of sensors 116. Channel separator 114 can be any optical apparatus for separating light beams according to the position of impingement of the light beams onto the separator (i.e., spatial separation). For example, channel separator 114 can be a total internal reflection channel separator and the like.

Each of sensors 116 coincides with a respective one of the different perspectives object images, and provides the data to a processor (not shown) for producing a stereoscopic image of object 118. Each of proximal periscope prisms 110, proximal objective lens assembly 112, channel separator 114 and sensors 116 are positioned at the proximal end of endoscope 100 and outside of the body of a patient. Therefore those elements are not subject to the physical constraints of minimally invasive surgery and can be of any size. That is, the size limitations of the portion of endoscope 100, which is inserted into the body of a patient, do not apply to any of proximal periscope prisms 110, proximal objective lens assembly 112, channel separator 114 and sensors 116 (i.e., together referred to as the imaging system). The size and resolution of sensors 116 can be increased to increase the Nyquist frequency of endoscope 100, thereby avoiding aliasing of the stereoscopic images.

Reference is now made to FIGS. 2A, 2B, 2C, 2D and 2E, which are schematic illustrations of a pair of distal periscope prisms, generally referenced 150, constructed and operative in accordance with another embodiment of the disclosed technique. Periscope prisms 150 include a first distal periscope prism 152 and a second distal periscope prism 154.

Figure 2A:
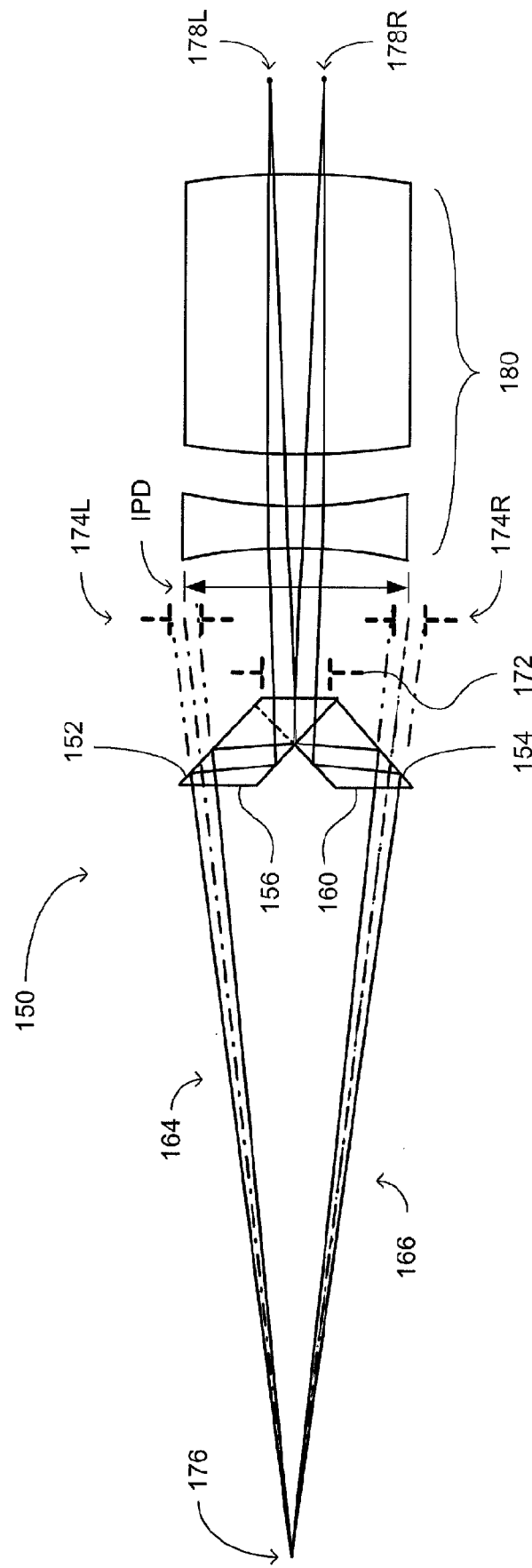
FIGS. 2A, 2B, 2C, 2D and 2E, are schematic illustrations of a pair of periscope prisms, constructed and operative in accordance with another embodiment of the disclosed technique.

FIG. 2A depicts distal periscope prisms pair 150 from a side view perspective. Light beams 164, corresponding to a first perspective of a point 176 of an object (e.g., object 118 of FIG. 1), impinges on an entrance surface 156 of first distal periscope prism 152. In a substantially similar manner, light beams 166, corresponding to a second perspective of the object, impinges on an entrance surface 160 of second distal periscope prism 154. Light beams 164 and 166 are transmitted through first prism 152 and second prism 154, respectively. Each of light beams 164 and 166 is further transmitted through an objective lens assembly 180. Light beams 164 converge together for producing a left image 178L of point 176 of the object. Light beams 166 converge together for producing a right image 178R of point 176 of the object.

The optical relay system (e.g., the relay system of FIG. 1) produces an image of (i.e., re-images) the pupils of the stereoscopic endoscope (e.g., the pupils of dual pupil 108) onto pupil plane image 172. Periscope prisms 150 re-image pupil plane image 172 onto pupils 174L and 174R. In particular, periscope prisms 150 re-image the left pupil of pupil plane image 172 onto re-imaged pupil 174L, and re-image the right pupil of pupil plane image 172 onto re-imaged pupil 174R. Thereby, only light beams reflected from the object toward re-imaged pupils 174L and 174R enter the optical relay system and eventually constitute the stereoscopic image pair. It is noted that the IPD of periscope prisms 150 is defined as the distance between the centers of a pair of re-imaged pupils 174L and 174R.

Figure 2E:
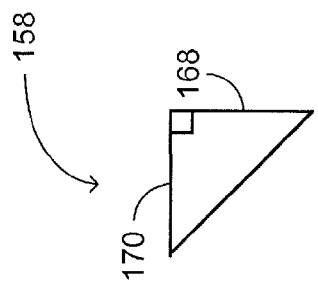
Figure 2D:
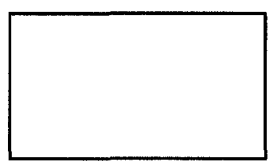
Figure 2C:
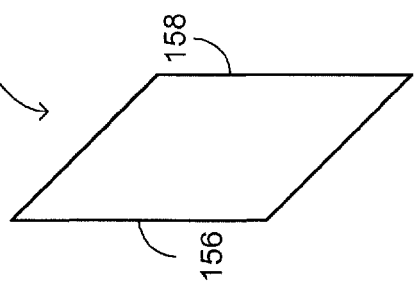
Figure 2B:
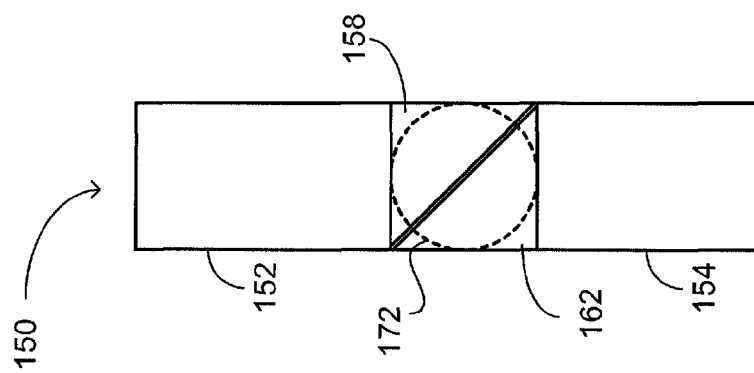

FIG. 2B depicts periscope prisms 150 from a front view perspective. Periscope prism 152 includes a triangular exit surface 158. Periscope prism 154 includes a triangular exit surface 162. Triangular exit surfaces 158 and 162 are positioned adjacent to each other, such that they complement each other and together form a square shape (not referenced).

A dotted circle 172 depicted on the square formed by exit surfaces 158 and 162, represents the shape of the dual pupil of the stereoscopic endoscope (e.g., dual pupil 108 of endoscope 100 of FIG. 1), as detailed further herein below with reference to FIG. 3. Thus, only the portions of light beams 164 and 166 transmitted through the area covered by dotted circle 172 would impinge on the dual pupil and would afterwards be detected by the sensors.

As can be seen from FIG. 2B, the boundary between the pupils of the dual pupil (i.e., represented by dotted circle 172) correspond to the chamfering of the exit surfaces of distal periscope prisms 152 and 154, and is diagonal. That is, as each of exit surfaces 158 and 172 is a chamfered at 45° degrees, the boundary is inclined at a corresponding angle of 45° degrees. In this manner, the dimension in the first principle axis (e.g., vertical axis) of each pupil is the same as the dimension in the second principle axis (e.g., horizontal axis). Thereby, the resolution in each of the principle axes of each pupil is similar. Alternatively, other chamfering angles of the exit surfaces of the distal periscope prisms are possible.

FIG. 2C is a side view perspective of first distal periscope prism 152 (which is similar to second prism 154). FIG. 2D is a side view perspective of entrance surface 156 of first distal periscope prism 152 (which is similar to entrance surface 160 of second prism 154). FIG. 2E is a front view perspective of an exit surface 158 of first distal periscope prism 152 (which is similar to exit surface 162 of second periscope prism 154).

As can be seen from FIG. 2E, the shape of exit surface 158 is a right angled triangle (i.e., exit surface 158 is chamfered). In particular, the ratio between the lengths of side walls 168 and 170 corresponds to the slope of the chamfers in each of prisms 152 and 154. This slope of the chamfers (i.e., the angle of inclination or inclination angle) is defining the ratio between vertical and horizontal dimension of each of the pupils, thereby defining the resolution of the channels of the endoscope, respective of the pupils, in horizontal and vertical directions. For example, an inclination angle of 30° corresponds with a sensor, which resolution ration (i.e., proportion) between the principle axes is 2. In particular, the resolution in the horizontal axis is twice as that in the vertical axis.

Alternatively, distal periscope prisms include more than two prisms for receiving more than two images of different perspectives of the object. The exit surfaces of the distal periscope prisms complement each other for forming together a square. Accordingly, the dual pupil is replaced with pupil assembly including one pupil for each of the periscope prisms. The shape of the opening in the aperture stop of the pupil assembly (i.e., the combined surface area of all the pupils) corresponds to the shape of the cross section of the optical relay system. That is, the combined surface area of all the pupils substantially fully forms the shape of the cross section of the relay system.

Figure 3:
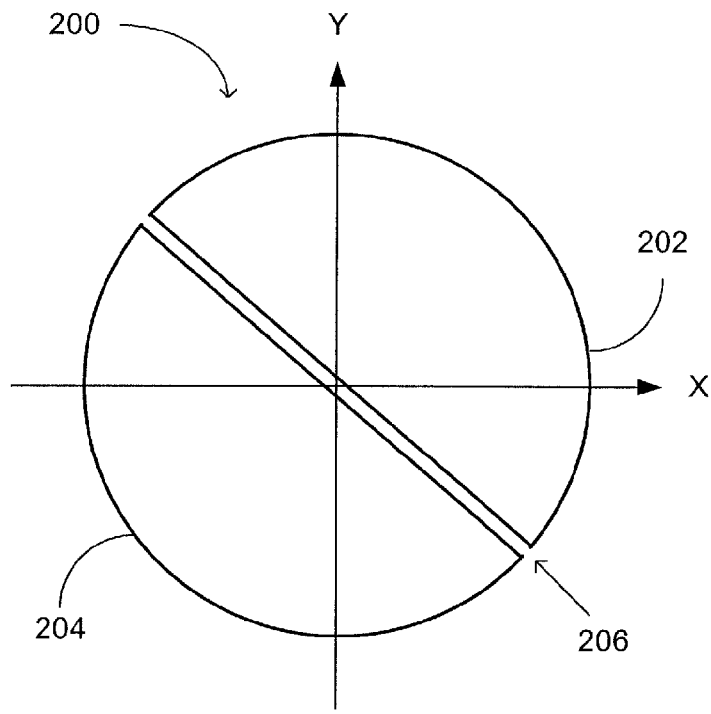
FIG. 3 is a schematic illustration of dual pupil, constructed and operative in accordance with a further embodiment of the disclosed technique.

Reference is now made to FIG. 3, which is a schematic illustration of a dual pupil, generally referenced 200, constructed and operative in accordance with a further embodiment of the disclosed technique. Dual pupil 200 includes a first channel pupil 202 and a second channel pupil 204 (e.g., left and right perspective pupils). Each of first channel pupil 202 and second channel pupil 204 is in the shape of half of a circle. First channel pupil 202 and second channel pupil 204 are positioned adjacent to each other and complement each other for forming together a full circle.

A diagonal line 206 marks the boundary between first channel pupil 202 and second channel pupil 204. The angle of diagonal line 206 with respect to the Y axis and with respect to the X axis (i.e., the principle axes) is 45° degrees. In this manner, the resolution of each of first channel having pupil 202 and second channel having pupil 204 is similar in both the Y axis (i.e., the vertical axis) and the X axis (the horizontal axis). Each of first channel pupil 202 and second channel pupil 204 receives light beams of a different perspective of the object for producing a stereoscopic image.

The pixel size of the sensor (e.g., sensors 116 of FIG. 1) should be appropriate to specific Nyquist criteria for avoiding aliasing of the image. The Nyquist frequency determining the pixel size is substantially about the spatial cutoff frequency of the optical system:

$$f_0 = \frac{1}{\lambda \times (f/\#)} \quad (1)$$

where '$f_0$' is the spatial cutoff frequency of the optical system, '$\lambda$' is the average wavelength of the light beams recorded (or absorbed) by the sensors 116, and '$f/\#$' is the $F_{number}$ of the optical system. It is noted that the beams reflected from the object have much larger spectrum than those recorded by the sensors. The size of the pixel, for avoiding aliasing, is proportional to the $F_{number}$ of the optical system. The $F_{number}$ of the optical system (e.g., endoscope 100) is inversely proportional to the size of each pupil of dual pupil 200. From all of the above, the maximal pixel size for avoiding aliasing is related to, and in particular decreases with, the size of the pupil.

As mentioned above, the dual pupil is re-imaged periodically along the optical relay system. The dual pupil image substantially fully occupies the cross section of the optical relay system in at least one location of the optical relay system. In this manner, the pupil size is maximal for given dimensions of the optical relay system cross section, thereby allowing higher spatial cutoff frequency (i.e., better effective resolution) of the system than with conventional pupils, such as circular pupils.

Figure 4:
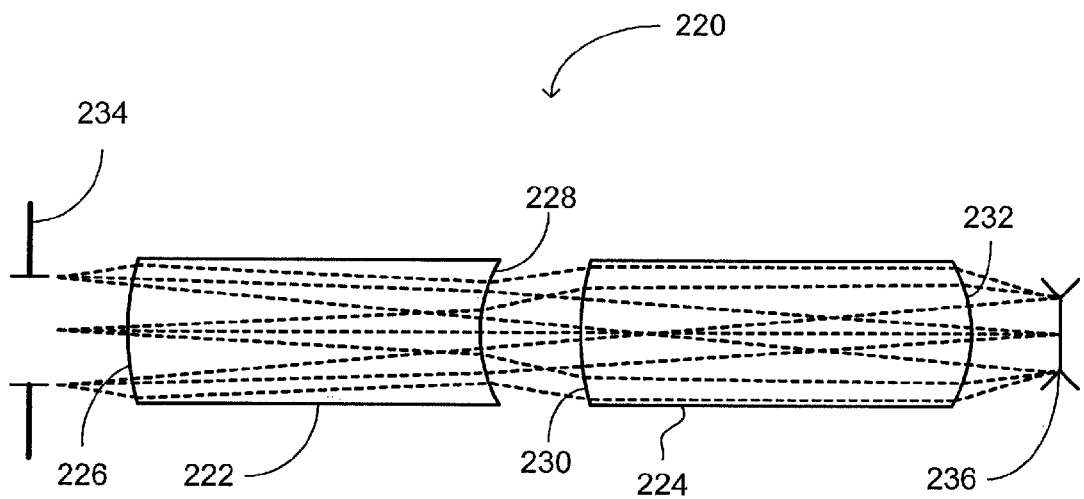
FIG. 4 is a schematic illustration of a rod lenses sub-chain, constructed and operative in accordance with another embodiment of the disclosed technique.

Reference is now made to FIG. 4, which is a schematic illustration of a rod lenses sub-chain, generally referenced 220, constructed and operative in accordance with another embodiment of the disclosed technique. Rod lenses sub-chain 220 includes a first rod 222 lens and a second rod lens 224. Rod lens 222 includes convex and concave surfaces 226 and 228, respectively. Rod lens 224 includes two convex surfaces 230 and 232. Rod lens 222 is positioned distally to rod lens 224, and is optically coupled therewith. That is, light beams exiting surface 228 of rod lens 222 enters rod lens 224 through surface 230.

As mentioned above, with reference to the optical relay system of FIG. 1, the dual pupil is periodically re-imaged by the optical relay system. The channels associated with each pupil are fully separated, on any one of the pupil plane images. In the example set forth in FIG. 4, an intermediate pupil plane 234 is positioned distally of rod lens sub-chain 220.

Depicted as dotted lines are exemplary light beams (not referenced) reflected from the object through the re-imaged pupils (not shown) of intermediate re-imaged pupil plane 234. The light beams constitute a first side view perspective of the object and a second side view perspective of the object (i.e., stereoscopic image pair). The light beams are transmitted through rod lenses 222 and 224 and converge onto an intermediate image 236. That is, the image of the object is reproduced in intermediate image 236.

As can be seen in FIG. 4, the exemplary light beams occupy substantially fully the cross section of rod lens 224. In particular, the dual pupil image, when relayed along the relay system, occupies substantially fully the cross section of the relay system, in at least one location along the relay system.

It is noted that, rod lenses sub-chain 220 forms a link in the rod lenses chain of the stereoscopic endoscope (e.g., rod lenses chain 106). Thus, the rod lenses chain is constructed of repeating sub-chains 220, as detailed further herein below with reference to FIG. 5. In this manner, a series of intermediate images of the object and a series of intermediate pupil planes are produced between adjacent rod lenses sub-chains.

Surfaces 226, 230 and 232 are converging surfaces and surface 228 is a diverging surface. In this manner, rod lenses sub-chain 220 maintains entering light beams within its diameter by employing a series of converging and diverging surfaces.

The negative optical power of concave surface 228 is substantially larger than positive optical power of convex surface 226. Therefore, the overall optical power of rod-lens 222 is substantially negative. Both convex surfaces 230 and 232 are of positive optical power and therefore the overall optical power of lens 224 is substantially positive. Assignment of the negative optical power of optical surface 228, together with proper choice of glass materials and radii, allows correction of all primary aberrations of sub-chain 200. Additionally, sub-chain 200 has a high Numerical Aperture value because of the short focal distance of sub-chain 220, constructed of rod-lenses 222 and 224.

The strong negative power of surface 228 decreases the Petzval sum of rod-lenses sub-chain 220 to substantially zero, thereby flattening the field curvature of intermediate image plane 236. Additionally, the strong negative power of surface 228 compensates for chromatic aberrations caused by surfaces 226, 230 and 232, of positive power, compensates for accumulated spherical and Coma aberrations, and decreases astigmatism and distortion. Sub-chain 220 including strong negative power surface 228 functions in a similar manner to that of a reverse telephoto lenses or a Cooke triplet lenses.

Figure 5:
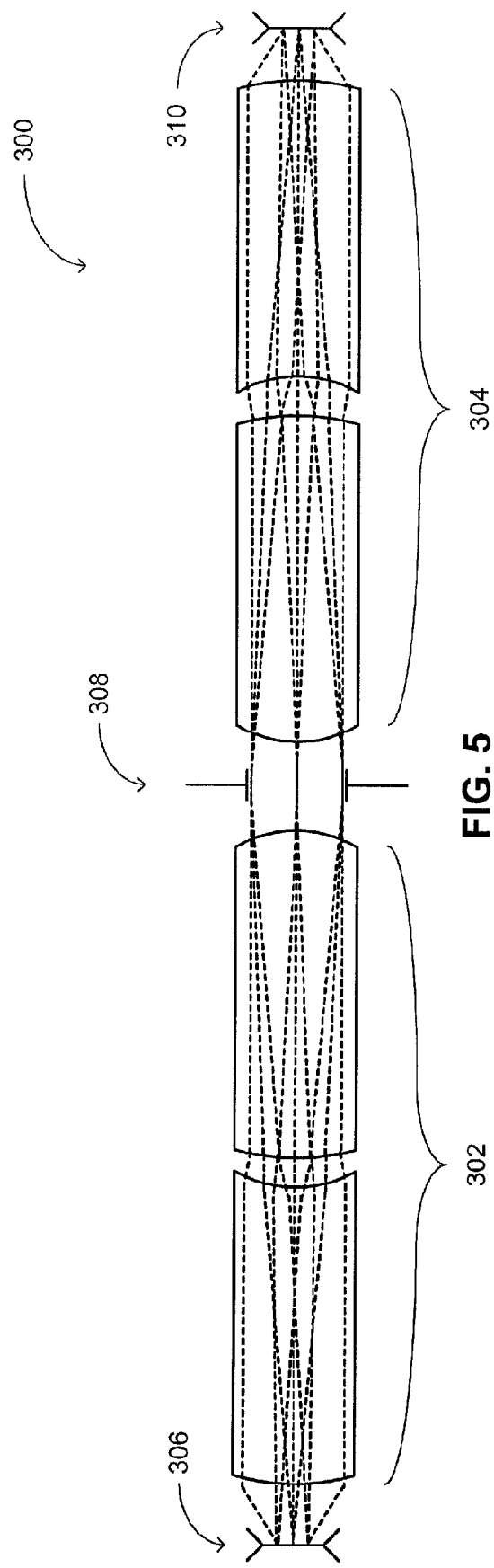
FIG. 5 is a schematic illustration of a pair rod lenses sub-chains, constructed and operative in accordance with a further embodiment of the disclosed technique.

Reference is now made to FIG. 5, which is a schematic illustration of a pair of rod lenses sub-chains, generally referenced 300, constructed and operative in accordance with a further embodiment of the disclosed technique. Rod lenses sub-chains pair 300 includes a first of a rod lenses sub-chain 302 and a second rod lenses sub-chain 304. Sub-chain 302 includes similar rod lenses (not referenced) to sub-chain 304. However, the lenses of sub-chain 304 are inversely ordered and inversely oriented. That is, the distal lens of sub-chain 302 is the proximal lens of sub-chain 304 inversely oriented (i.e., the left surface is facing to the right and the right surface is facing to the left). Put another way, the structure of sub-chain 304 is a mirror image of the structure of sub-chain 302.

Sub-chains 302 and 304, together with a plurality of additional similar sub-chains constitute the rod lenses chain of a stereoscopic endoscope. A series of images of the object and a series of pupil planes are repeatedly produced by the rod lenses chain (i.e., object imaging and pupil imaging). In the example set forth in FIG. 5, an $N^{th}$ intermediate image 306 is positioned distally to sub-chain 302, an $N^{th}$ intermediate pupil plane 308 is positioned between sub-chain 302 and sub-chain 304 and an $(N+1)^{th}$ intermediate image 310 is positioned proximally to sub-chain 304. That is, light reflected from the object, travels from the direction of $N^{th}$ intermediate image 306 through sub-chain 302, $N^{th}$ intermediate pupil plane 308 and sub-chain 304 toward $(N+1)^{th}$ intermediate image 310). $(N+1)^{th}$ intermediate image 310 is re-imaging of $N^{th}$ intermediate image 306 by rod-lenses chains 302 and 304.

As detailed herein above, the different optical channels (i.e., respective of the different pupils) are fully separated at each of the intermediate pupil planes. Therefore, a channels combiner or a channels separator should be positioned at the position of a respective one of the pupil planes. In a similar manner, the aperture stop (i.e., the dual pupil) is also positioned on a respective one of the pupil planes. The sensors are positioned on a respective object image.

Reference is now made to FIG. 6A, which is a schematic illustration of a stereoscopic endoscope system, generally referenced 350, constructed and operative in accordance with another embodiment of the disclosed technique. Endoscope 350 includes a pair of distal periscope prisms 352, a distal object lens assembly 354, a rod lenses chain 356, a dual pupil 358, a pair of proximal periscope prisms 360, proximal objective lens assemblies 362, and a pair of sensors 366.

Each of distal periscope prisms pair 352, distal objective lens assembly 354, and proximal periscope prisms pair 360, is substantially similar to distal periscope prisms pair 102, distal objective lens assembly 104, and proximal periscope prisms pair 110, of FIG. 1, respectively.

Sensors 366 are similar to sensors 116 of FIG. 1, but are positioned differently. Sensors 366 are positioned parallel to each other. Proximal objective lens assemblies 362 are positioned between proximal periscope prisms pair 360 and sensors 366 for re-forming the images on said sensors 366. Alternatively, sensors 366 can be positioned in various locations as long as each receives images from different pupil of dual pupil 358.

Further alternatively, endoscope 350 includes a three-dimensional (3D) sensor instead of the pair of sensors 366. The 3D sensor receives both images and detects each image separately, such that a stereoscopic image can be produced therefrom. For example, the 3D sensor includes a layer of micro lenses separating between the images for enabling the 3D sensor to detect the images separately.

Rod lenses chain 356 includes a plurality of rod lenses sub-chains (not shown). Rod lenses chain 356 relays the stereoscopic image pair with reduced aberrations by having a long focal length and by employing repeating sub-chains composed of diverging and converging rod lenses. Rod lenses chain 356 produces a series of object images and a series of pupil plane images. Dual pupil 358 is positioned on one such intermediate pupil plane image in the middle of rod lenses chain 356.

Channel separator 364 is a folding element directing a first channel (associated with a first pupil) onto a first sensor, and directing a second channel (associated with a second pupil) onto a second sensor. Channel separator is positioned such that the channels are fully separated thereby, substantially without crosstalk.

Reference is now made to FIG. 6B, which is schematic illustration of a front side view of one of the sensors of the endoscope of FIG. 6A. Sensor 366 is rectangular shaped. The dimensions of sensor 366 are given by side walls 370 and 372.

Reference is now made to FIG. 6C, which is a schematic illustration of a front side view of the complementing exit surfaces of the distal periscope prisms of the endoscope of FIG. 6A. Exit surfaces 374 and 376 are right angled triangles. Accordingly, the boundary between the pupils of the dual pupil (the dual pupil is represented by dotted circle 382), is inclined at a corresponding angle. In particular, the ratio between the lengths of side walls 378 and 380 corresponds to the slope of the chamfers in each of prisms 352. This slope is defining the ratio between vertical and horizontal dimension of each half-pupil, which consequently relates to final resolution of both channels in horizontal and vertical directions.

Figure 7C:
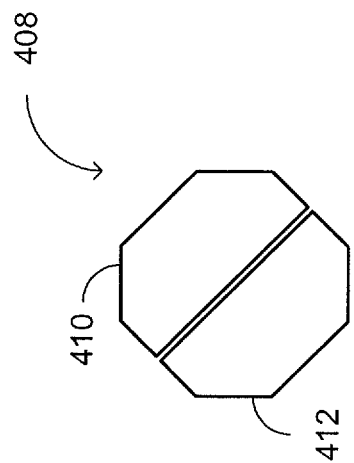
FIGS. 7A, 7B and 7C, are schematic illustrations of various components of an optical relay system, constructed and operative in accordance with a further embodiment of the disclosed technique.
Figure 7B:
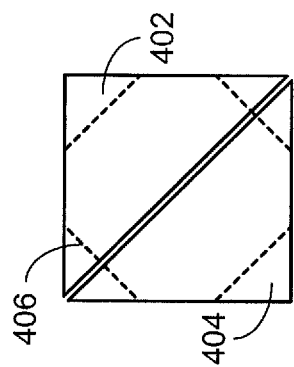
Figure 7A:
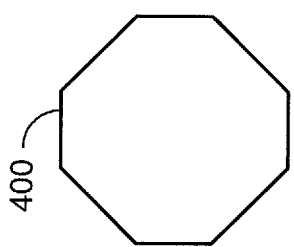

Reference is now made to FIGS. 7A, 7B and 7C, which are schematic illustrations of components of an optical relay system, constructed and operative in accordance with a further embodiment of the disclosed technique. FIG. 7A depicts the cross-section of a rod lens 400 of the rod lenses chain of a stereoscopic endoscope (e.g., rod lenses chain 106 of FIG. 1). The cross-section shape of rod lens 400 is octagonal.

FIG. 7B depicts the complementing exit surfaces of a pair of distal periscope prisms of the stereoscopic endoscope (e.g., periscope prisms 102). Chamfered exit surfaces 402 and 404 are positioned adjacent to each other such that they complement each other and together form a full square. Dotted octagon 406 represents the re-imaged dual pupil of the endoscope.

FIG. 7C depicts dual pupil 408 of the stereoscopic endoscope. The shape of dual pupil 408 (I.e., the shape of the opening of the aperture stop of dual pupil 408) corresponds to that of the cross-section shape of the relay system.

Additionally, the image of dual pupil 408 substantially completely covers the cross section of the relay system, in at least one location along the relay system. Dual pupil 408 includes two complementing pupils 410 and 412. The boundary between pupils 410 and 412 is determined such that the resolution of each pupil in each of the principle axes corresponds to the resolution of the sensor.

In the endoscopes presented herein above (e.g., with reference to FIGS. 1 and 6A), all components of the distal objective lens assembly of the endoscope system are positioned proximally to the distal periscope prisms. That is, light reflected from the object passes first through the distal periscope prisms, and only afterwards reaches the common distal objective lens assembly. As detailed herein below, with reference to FIGS. 8A-8D, the distal periscope prisms may produce vignetting effect, thereby effectively limiting the Field of View (FOV) of the endoscope system. Put another way, light arriving to the distal periscope prisms at a too acute angle, would not reach the common distal objective lens assembly. Note that the common distal objective lens assembly is shared by both optical channels—right and left—and is therefore referred to as common.

In accordance with another embodiment of the disclosed technique, the distal objective lens assembly includes a common lens assembly, a left lens assembly and a right lens assembly. The common lens assembly is positioned proximally to the distal periscope prisms. The right and left lens assemblies are parallel to each other, and are both positioned distally of the distal periscope prisms.

Each of the left and the right lens assemblies re-images the respective portion of the dual pupil at the distal end thereof. In particular, the left lens assembly re-images the left pupil at a point which is distal thereto, and the right lens assembly re-images the right pupil at a point which is distal thereto. Thus, the re-imaged pupils are positioned at the distal end of the endoscope system (i.e., at the front of the endoscope system). Thereby, the field of view of the endoscope system having the right and left lens assemblies (e.g., endoscope 450 of FIG. 8A) is larger than that of the endoscope system having only a common objective lens assembly (e.g., endoscope 100 of FIG. 1).

Figure 8A:
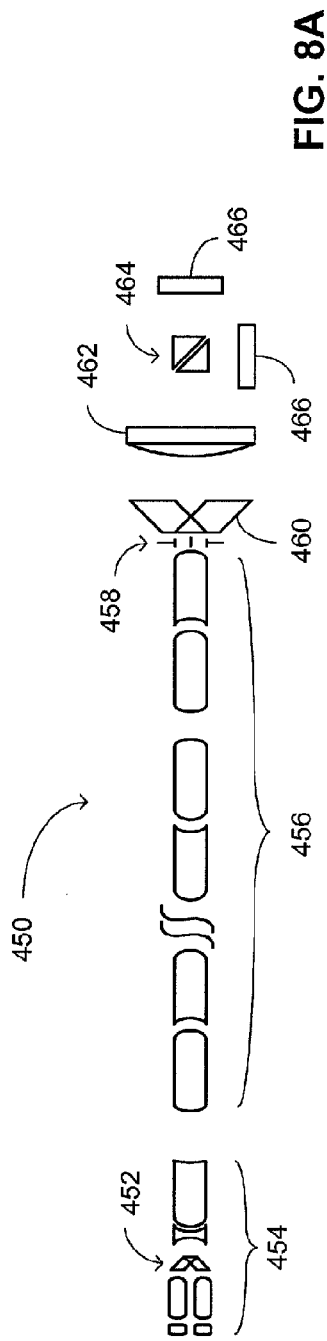
FIG. 8A is a schematic illustration of a stereoscopic endoscope, constructed and operative in accordance with another embodiment of the disclosed technique.
Figure 8B:
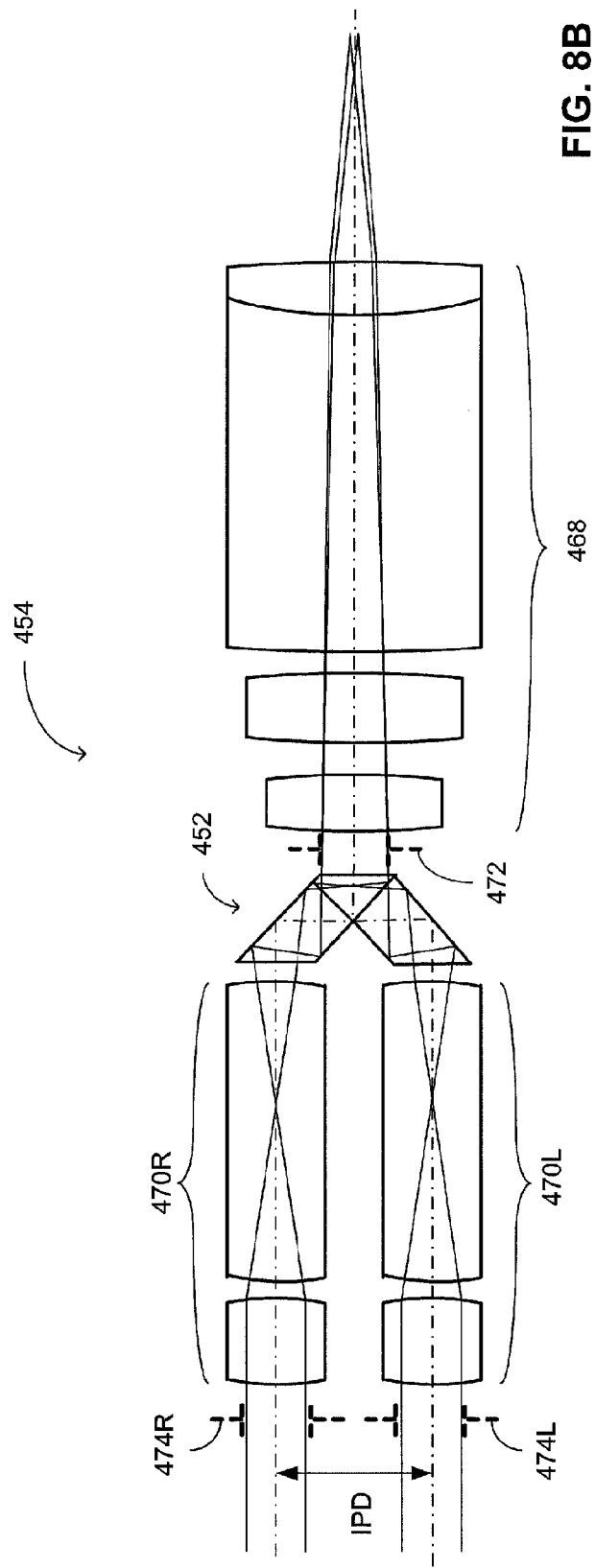
FIG. 8B is an enlarged view of the distal objective lens assembly of the endoscope of FIG. 8A.
Figure 8C:
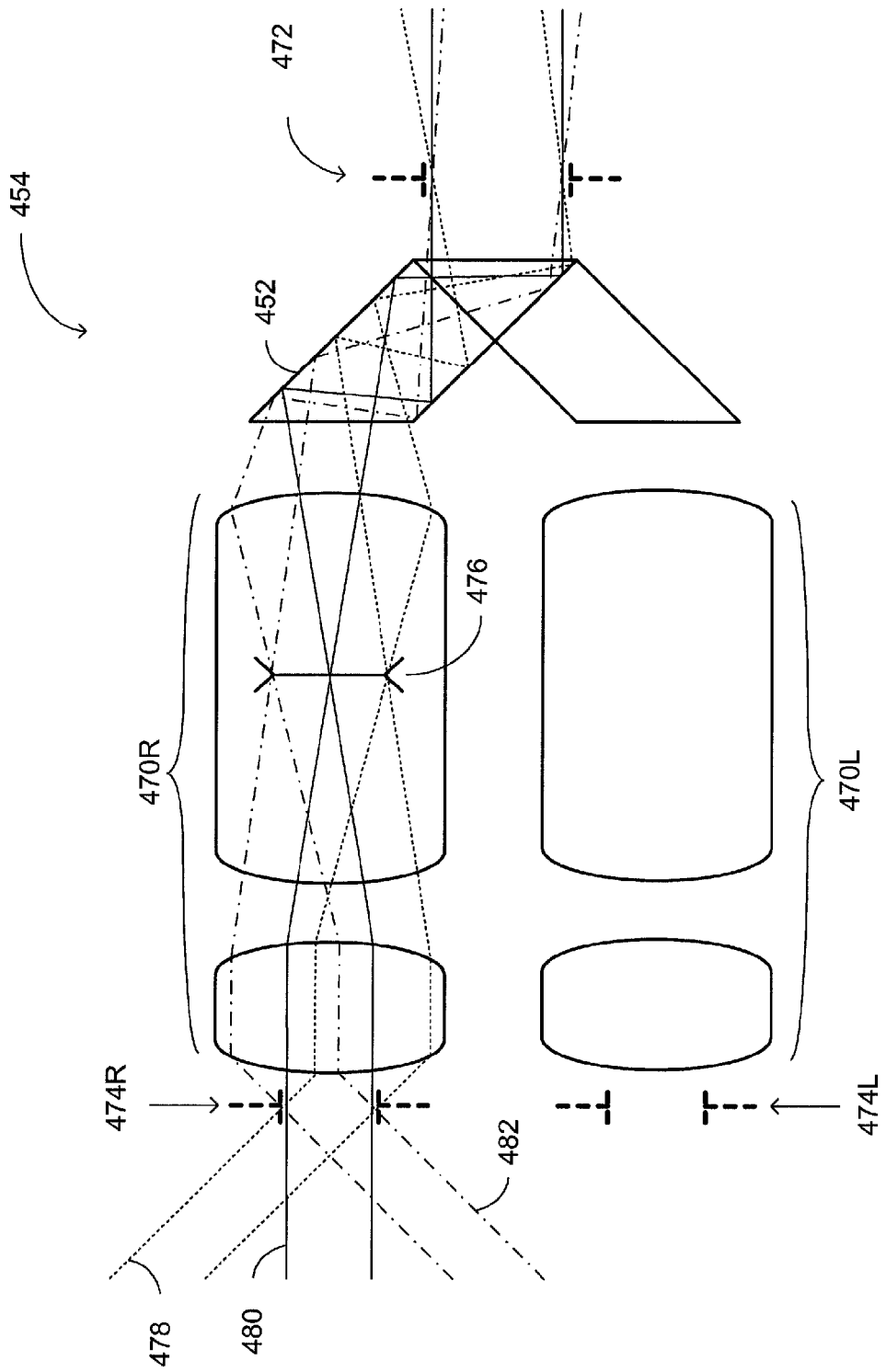
FIG. 8C is a schematic illustration of a ray diagram (i.e., ray tracing) within the right lens assembly of the distal objective lens assembly of FIG. 8B.
Figure 8D:
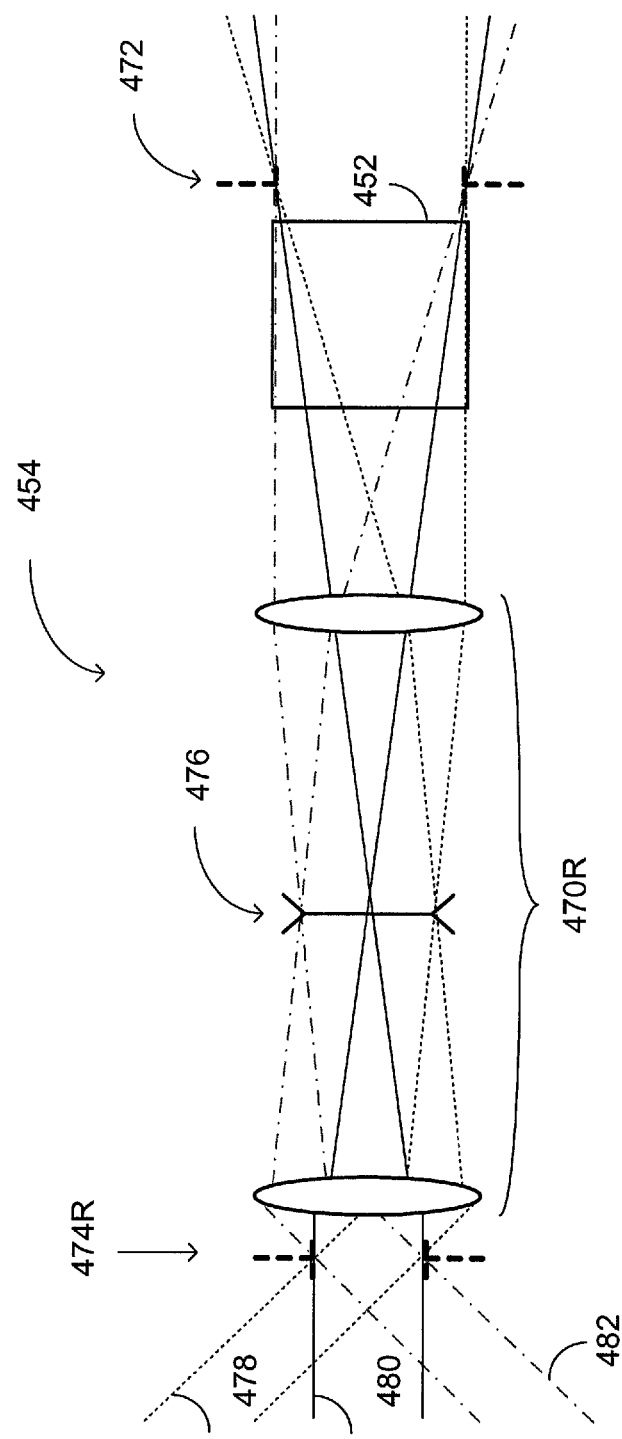
FIG. 8D is a schematic illustration of an equivalent ray tracing, which is equivalent to the ray tracing of the right lens assembly of FIG. 8C.

Reference is now made to FIGS. 8A, 8B 8C, and 8D. FIG. 8A is a schematic illustration of a stereoscopic endoscope, generally referenced 450, constructed and operative in accordance with another embodiment of the disclosed technique. FIG. 8B, is an enlarged view of the distal objective lens assembly of the endoscope of FIG. 8A. FIG. 8C is a schematic illustration of a ray diagram (i.e., ray tracing) within the right lens assembly of the distal objective lens assembly of FIG. 8B. FIG. 8D is a schematic illustration of an equivalent ray tracing, which is equivalent to the ray tracing (i.e., optical path) of the right lens assembly of FIG. 8C.

With reference to FIG. 8A, endoscope 450 includes a pair of distal periscope prisms 452, distal objective lens assembly 454, a relay system 456 (e.g., a rod lenses chain 456), a dual pupil 458, a pair of proximal periscope prisms 460, a proximal objective lens assembly 462, a channel separator 464, and two sensors 466. Each of pair of distal periscope prisms 452, rod lenses chain 456, dual pupil 458, pair of proximal periscope prisms 460, proximal objective lens assembly 462, channel separator 464, and two sensors 466, is substantially similar to each of pair of distal periscope prisms 102, rod lenses chain 106, dual pupil 108, pair of proximal periscope prisms 110, proximal objective lens assembly 112, channel separator 114, and two sensors 116, of FIG. 1, respectively.

With reference to FIG. 8B, distal objective lens assembly 454 includes a common lens assembly 468 a right lens assembly 470R and a left lens assembly 470L. Common lens assembly 468 is positioned proximally of distal prisms 452. Right and left lens assemblies 470R and 470L are parallel to each other, and both are positioned distally of distal prisms 452.

Right and left lens assemblies 470R and 470L enable endoscope 450 to receive a wider FOV, than the FOV detected by endoscope 100 of FIG. 1. Each of the pair of the parallel lens assemblies (i.e., right and left lens assemblies 470R and 470L) re-images the respective pupil of dual pupil 458 at a point distal to objective lens assembly 454. That is, left lens assembly 470L re-images the left pupil as re-imaged left pupil 474L, and right lens assembly 470R re-images the right pupil as re-imaged right pupil 474R. The re-imaged pupils 474R and 474L, positioned at the distal end of endoscope 450, allows to enlarge the FOV of endoscope 450 with respect to that of endoscope 100, in which the re-imaged pupils were positioned proximally to the distal prisms. Additionally, each of the pair of parallel lens assemblies forms an image of the detected object, and directs the image toward common lens assembly 468.

Common lens assembly 468 re-images dual pupil 458 as re-imaged dual pupil 472. Additionally, common lens assembly 468 re-images the images of the detected object, formed by right and left lens assemblies 470R and 470L, and directs the images toward common relay system 456 of FIG. 8A (e.g., rod lenses chain 456). Note that FIG. 8B depicts the IPD of endoscope 450, which is defined by the distance between re-imaged pupils 474R and 474L.

With reference to FIG. 8C, right lens assembly 470R, and left lens assembly 470L are depicted in an enlarged view. FIG. 8C further depicts an exemplary ray tracing (i.e., ray diagram), including three beams of light rays 478, 480 and 482, arriving to right lens assembly 470R from three different directions. Light beam 478 is depicted as a dotted line, light beam 480 is depicted as a full line, and light beam 482 is depicted as a dot-dashed line. Light beams 478, 480 and 482 are all detected by endoscope 450 (FIG. 8A) and represent a wide FOV. It is further noted that the exemplary ray tracing is only depicted for right lens assembly 470R, but similar ray tracing is also applicable to left lens assembly 470L.

Common lens assembly 468 (FIG. 8B) re-images dual pupil 458 (FIG. 8A) as re-imaged dual pupil 472, which is positioned proximally to distal periscope prisms 452. Additionally, right lens assembly 470R re-images the right pupil of dual pupil 458 as re-imaged right pupil 474R, which is positioned distally to right objective lens assembly 470R. That is, re-imaged right pupil 474R is positioned at the distal end of endoscope 450. In a similar manner, left objective lens assembly 470L re-images the left pupil of dual pupil 458 as re-imaged left pupil 474L, which is positioned distally to right objective lens assembly 470R at the distal end of endoscope 450.

Right objective lens assembly 470R forms an intermediate image 476 of the detected object (not shown) there-within. In a similar manner, left objective lens assembly 470L forms an intermediate image (not shown) of the detected object there-within. For forming a real image of the detected object, each of right distal objective lens assembly 470R, and left distal objective lens assembly 470L includes at least one positive power lens. In the example set forth in FIGS. 8A, 8B, 8C and 8D, both lenses (not referenced) of each of right and left lens assemblies 470R and 470L, are positive power lenses. That is, right and left lens assemblies 470R and 470L include no negative power optical components. Alternatively, one or more of the lenses of right and left distal objective lens assemblies 470R and 470L can be a negative power lens (i.e., as long as at least one of the lenses is a positive power lens).

FIG. 8D depicts an equivalent ray tracing (i.e., ray diagram or light path), which is equivalent to the ray tracing of FIG. 8C. That is, the light rays depicted in FIG. 8D represent the light rays depicted in FIG. 8C, and the optical elements depicted in FIG. 8D represent those of FIG. 8C. Put another way, FIG. 8D represents the optical path of light rays 478, 480 and 482 through right distal objective lens assembly 470R laid out in a flattened manner, such that it is easier to see the re-imaged pupils and the formed images of the detected object.

FIG. 8D depicts an equivalent of right distal objective lens assembly 470R and of distal prism 454. FIG. 8D further depicts an equivalent of light beams 478, 480 and 482. Looking at the path of beams, 478, 480 and 482, one can identify re-imaged right pupil 474R, re-imaged dual pupil 472 (i.e., composed of a re-imaged right pupil and a re-imaged left pupil), and an intermediate image 476 of the detected object (not shown). As mentioned above, re-imaged right and left pupils 474R and 474L, positioned at the distal end of endoscope 450 (FIG. 8A), enable endoscope 450 to detect a wider FOV than endoscope 100 (FIG. 1).

As depicted in FIG. 8D, the footprint of light detected by endoscope 450 (FIG. 8A), as represented by light beams 478, 480 and 482, is the same size as re-imaged right pupil 474R, and re-imaged dual pupil 454. Therefore, the footprint of light detected by endoscope 450 is the same size as dual pupil 458. In particular, the footprint of light passing through the right objective lens assembly is the same size as the right pupil, and the footprint of fight passing through the left objective lens assembly is the same size as the left pupil. In other words, the beam wandering of light detected by endoscope 450 does not exceed dual pupil 458, and therefore endoscope 450 does not exhibit (i.e., does not produce) vignetting.

It will be appreciated by persons skilled in the art that the disclosed technique is not limited to what has been particularly shown and described hereinabove. Rather the scope of the disclosed technique is defined only by the claims, which follow.

The invention claimed is:

1. A stereoscopic endoscope, comprising:
a dual pupil, comprising a first pupil and a second pupil positioned adjacent to each other, each of said first pupil and said second pupil receiving an image of a respective perspective of an object;
an optical relay system, said optical relay system having a proximal end and a distal end, optically coupled with said dual pupil at said proximal end, for relaying said respective images of said object, a cross section of said optical relay system having a first predetermined closed two-dimensional shape;
at least two distal periscope prisms, optically coupled with said distal end of said optical relay system, exit surfaces of each of said at least two distal periscope prisms being positioned adjacent to one another and geometrically complementing each other; and
a distal objective lens assembly, said distal objective lens assembly comprising:
a common lens assembly being positioned proximally to said at least two distal periscope prisms; and
a first front lens assembly and a second front lens assembly, both being positioned distally to said at least two distal periscope prisms,
wherein said first pupil and said second pupil each have a respective shape covering a different unique portion of said first closed two-dimensional shape;
wherein said respective shapes of said first pupil and said second pupil are complementary in shape and together form a second closed two-dimensional shape;
wherein said second closed two-dimensional shape substantially fully covers a surface area of said first closed two-dimensional shape when said first pupil and said second pupil are positioned adjacent to each other;
wherein each of said first front lens assembly and said second front lens assembly comprises at least one lens having positive power; and
wherein each of said first front lens assembly and said second front lens assembly forms an image of said object therewithin.

2. The stereoscopic endoscope according to claim 1, wherein said first front lens assembly re-images said first pupil at said distal end of said optical relay system, and wherein said second lens front assembly re-images said second pupil at said distal end of said optical relay system.

3. The stereoscopic endoscope according to claim 1, wherein said common lens assembly re-images said dual pupil between said common lens assembly and said at least two distal periscope prisms, and wherein said common lens assembly re-images images of said object therewithin.

4. The stereoscopic endoscope according to claim 3, wherein a footprint of light detected by said stereoscopic endoscope has a same size as said re-imaged dual pupil re-imaged by said common lens assembly.

5. The stereoscopic endoscope according to claim 1, wherein said optical relay system produces at least one image of a plane of said dual pupil, and wherein said dual pupil image substantially fully covers said surface area of said cross section of said optical relay system.

6. The stereoscopic endoscope according to claim 1, further comprising at least one sensor associated with each of said first pupil and said second pupil,
wherein for a selected sensor of said at least one sensor a ratio between a resolution in each of the principle axes of said selected sensor corresponds to a ratio between the dimensions in each of the principle axes of one of said first pupil and said second pupil being associated with said selected sensor.

7. The stereoscopic endoscope according to claim 6, wherein said at least one sensor is positioned in an external portion of said stereoscopic endoscope, said external portion not being inserted into a body of a patient during operation of said stereoscopic endoscope.

8. The stereoscopic endoscope according to claim 1, wherein said optical relay system comprises at least two identical sub-chains of rod lenses, each rod lens sub-chain comprising at least two rod lenses, wherein a selected one of said at least two rod lenses has negative optical power.

9. The stereoscopic endoscope according to claim 1, wherein a boundary between said exit surfaces of each of said at least two distal periscope prisms defines a boundary between said first pupil and said second pupil.

10. The stereoscopic endoscope according to claim 1, wherein said optical relay system forms therewithin at least one intermediate image of said object, and wherein said optical relay system re-images therewithin said dual pupil.

* * * * *